(12) United States Patent
Cook et al.

(10) Patent No.: US 8,920,515 B2
(45) Date of Patent: Dec. 30, 2014

(54) GRAFT PROSTHESIS, MATERIALS AND METHODS

(75) Inventors: William A. Cook, Bloomington, IN (US); Michael C. Hiles, Lafayette, IN (US); Thomas G. Kozma, McHenry, IL (US); Umesh H. Patel, West Lafayette, IN (US)

(73) Assignees: Cook Biotech Incorporated, West Lafayette, IN (US); Cook Medical Technologies LLC, Bloomington, IN (US)

( * ) Notice: Subject to any disclaimer, the term of this patent is extended or adjusted under 35 U.S.C. 154(b) by 898 days.

(21) Appl. No.: 11/931,811

(22) Filed: Oct. 31, 2007

(65) Prior Publication Data

US 2008/0171092 A1 Jul. 17, 2008
US 2010/0104658 A2 Apr. 29, 2010

Related U.S. Application Data (60) Continuation of application No. 10/811,343, filed on Mar. 26, 2004, now Pat. No. 7,652,077, which is a (Continued)

(51) Int. Cl.
*A61F 2/02* (2006.01)
*A61L 27/24* (2006.01)

(Continued)

(52) U.S. Cl.
CPC ............. *A61L 27/24* (2013.01); *A61L 2/0088* (2013.01); *A61L 27/3604* (2013.01); *A61L 27/3662* (2013.01); *A61L 27/3683* (2013.01);

(Continued)

(58) Field of Classification Search
USPC ......... 523/105, 113; 623/23.75, 23.71, 23.61, 623/924–925; 8/94.11; 530/356; 424/551, 424/426

See application file for complete search history.

(56) References Cited

U.S. PATENT DOCUMENTS

| 2,172,903 A | 9/1939 | Charping |
| 3,346,401 A | 10/1967 | Barat et al. |

(Continued)

FOREIGN PATENT DOCUMENTS

| EP | 0405429 | 1/1991 |
| GB | 2266239 | 10/1993 |

(Continued)

OTHER PUBLICATIONS

Meyer-Rosberg et al, "Helicobacter Colonization of Biopsy Specimens in Vitro . . . ", Scand. J. Gastroenterology 1996:434-441, (May 1996).*

(Continued)

*Primary Examiner* — Paul Prebilic
(74) *Attorney, Agent, or Firm* — Woodard, Emhardt, Moriarty, McNett & Henry LLP (57) ABSTRACT

A graft prostheses (11), materials and method for implanting, transplanting, replacing, or repairing a part of a patient. The graft prosthesis includes a purified, collagen-based matrix structure removed from a submucosa tissue source. The submucosa tissue source is purified by disinfection and removal steps to deactivate and remove contaminants, thereby making the purified structure biocompatible and suitable for grafting on and/or in a patient.

25 Claims, 1 Drawing Sheet

Related U.S. Application Data continuation of application No. 09/798,441, filed on Mar. 2, 2001, now abandoned, which is a division of application No. 08/916,490, filed on Aug. 22, 1997, now Pat. No. 6,206,931.

(60) Provisional application No. 60/024,542, filed on Aug. 23, 1996, provisional application No. 60/024,693, filed on Sep. 6, 1996.

(51) Int. Cl.
*A61L 2/00* (2006.01)
*A61L 27/36* (2006.01)
*A61L 27/38* (2006.01)
*A61L 29/00* (2006.01)
*A61L 31/00* (2006.01)
*A61F 2/06* (2013.01)
*A61F 2/07* (2013.01)

(52) U.S. Cl.
CPC ........ *A61L 27/3695* (2013.01); *A61L 27/3839* (2013.01); *A61L 27/3843* (2013.01); *A61L 27/386* (2013.01); *A61L 29/005* (2013.01); *A61L 31/005* (2013.01); *A61F 2/06* (2013.01); *A61F 2/07* (2013.01); *Y10S 623/925* (2013.01)
USPC ..... 623/23.75; 523/105; 623/925; 623/23.71; 623/23.72; 623/925

(56) References Cited

U.S. PATENT DOCUMENTS

| | | |
|---|---|---|
| 3,562,820 A | 2/1971 | Bernhard |
| 3,632,361 A | 1/1972 | Battista |
| 3,649,163 A | 3/1972 | McCusker |
| 3,810,473 A | 5/1974 | Cruz et al. |
| 4,193,813 A | 3/1980 | Chvapil |
| 4,292,972 A | 10/1981 | Pawelchak et al. |
| 4,320,201 A | 3/1982 | Berg et al. |
| 4,347,234 A | 8/1982 | Wahlig et al. |
| 4,394,370 A | 7/1983 | Jefferies |
| 4,404,970 A | 9/1983 | Sawyer |
| 4,409,332 A | 10/1983 | Jefferies et al. |
| 4,412,947 A | 11/1983 | Cioca |
| 4,421,947 A | 12/1983 | Kyle |
| 4,472,840 A | 9/1984 | Jefferies |
| 4,578,067 A | 3/1986 | Cruz, Jr. |
| 4,606,337 A | 8/1986 | Zimmermann et al. |
| 4,681,588 A | 7/1987 | Ketharanathan |
| 4,755,593 A | 7/1988 | Lauren |
| 4,798,611 A | 1/1989 | Freeman |
| 4,801,299 A | 1/1989 | Brendel et al. |
| 4,813,958 A | 3/1989 | Dixon |
| 4,837,379 A | 6/1989 | Weinberg |
| 4,838,888 A | 6/1989 | Nashef |
| 4,885,005 A | 12/1989 | Nashef et al. |
| 4,891,359 A | 1/1990 | Saferstein et al. |
| 4,902,508 A | 2/1990 | Badylak et al. |
| 4,925,924 A | 5/1990 | Silver et al. |
| 4,948,540 A | 8/1990 | Nigam |
| 4,950,483 A | 8/1990 | Ksander et al. |
| 4,956,178 A | 9/1990 | Badylak et al. |
| 4,969,912 A | 11/1990 | Kelman et al. |
| 4,970,298 A | 11/1990 | Silver et al. |
| 4,976,733 A | 12/1990 | Girardot |
| 4,994,084 A | 2/1991 | Brennen |
| 5,024,841 A | 6/1991 | Chu et al. |
| 5,028,695 A | 7/1991 | Eckmayer et al. |
| 5,071,436 A | 12/1991 | Huc et al. |
| 5,094,661 A | 3/1992 | Levy et al. |
| 5,106,949 A | 4/1992 | Kemp et al. |
| 5,141,747 A | 8/1992 | Scholz |
| 5,171,574 A | 12/1992 | Kuberasampath et al. |
| 5,206,023 A | 4/1993 | Hunziker |
| 5,206,028 A | 4/1993 | Li |
| 5,215,541 A | 6/1993 | Nashef et al. |
| 5,219,576 A | 6/1993 | Chu et al. |
| 5,256,418 A | 10/1993 | Kemp |
| 5,275,826 A | 1/1994 | Badylak et al. |
| 5,279,612 A | 1/1994 | Eberhardt |
| 5,281,422 A * | 1/1994 | Badylak et al. ............ 623/13.11 |
| 5,298,222 A | 3/1994 | O'Leary |
| 5,336,616 A * | 8/1994 | Livesey et al. ................ 435/395 |
| 5,352,463 A | 10/1994 | Badylak et al. |
| 5,368,608 A | 11/1994 | Levy et al. |
| 5,372,821 A | 12/1994 | Badylak et al. |
| 5,374,515 A | 12/1994 | Parenteau et al. |
| 5,397,352 A | 3/1995 | Burres |
| 5,411,887 A | 5/1995 | Sjolander |
| 5,413,791 A | 5/1995 | Rhee et al. |
| 5,437,287 A | 8/1995 | Phillips et al. |
| 5,437,962 A | 8/1995 | Jain et al. |
| 5,445,833 A | 8/1995 | Badylak et al. |
| 5,446,462 A | 8/1995 | Cleveland |
| 5,447,536 A | 9/1995 | Girardot et al. |
| 5,451,406 A | 9/1995 | Lawin et al. |
| 5,456,693 A | 10/1995 | Conston et al. |
| 5,457,093 A | 10/1995 | Cini et al. |
| 5,460,962 A | 10/1995 | Kemp |
| 5,466,462 A | 11/1995 | Rosenthal et al. |
| 5,476,516 A | 12/1995 | Seifter et al. |
| 5,480,424 A | 1/1996 | Cox |
| 5,480,427 A | 1/1996 | Kelman et al. |
| 5,489,022 A | 2/1996 | Baker |
| 5,489,261 A | 2/1996 | Franzblau et al. |
| 5,498,420 A | 3/1996 | Mentrup et al. |
| 5,501,706 A | 3/1996 | Arenberg |
| 5,507,810 A | 4/1996 | Prewett et al. |
| 5,510,121 A | 4/1996 | Rhee et al. |
| 5,510,418 A | 4/1996 | Rhee et al. |
| 5,512,291 A | 4/1996 | Li |
| 5,514,181 A | 5/1996 | Light et al. |
| 5,516,395 A | 5/1996 | Anhauser et al. |
| 5,520,925 A | 5/1996 | Maser |
| 5,522,840 A | 6/1996 | Krajicek |
| 5,531,786 A | 7/1996 | Perry et al. |
| 5,531,791 A | 7/1996 | Wolfinbarger |
| 5,554,389 A | 9/1996 | Badylak et al. |
| 5,565,210 A | 10/1996 | Rosenthal et al. |
| 5,567,806 A | 10/1996 | Abdul-Malak et al. |
| 5,571,181 A | 11/1996 | Li |
| 5,607,476 A | 3/1997 | Prewett et al. |
| 5,607,590 A | 3/1997 | Shimizu |
| 5,641,518 A | 6/1997 | Badylak et al. |
| 5,645,860 A | 7/1997 | Knapp et al. |
| 5,693,085 A | 12/1997 | Buirge et al. |
| 5,695,998 A * | 12/1997 | Badylak et al. ................ 435/391 |
| 5,707,962 A | 1/1998 | Chen et al. |
| 5,711,969 A | 1/1998 | Patel et al. |
| 5,733,337 A | 3/1998 | Carr, Jr. et al. |
| 5,755,791 A | 5/1998 | Whitson et al. |
| 5,762,966 A | 6/1998 | Knapp et al. |
| 5,782,914 A | 7/1998 | Schankereli |
| 5,866,414 A | 2/1999 | Badylak et al. |
| 5,885,619 A | 3/1999 | Patel et al. |
| 5,955,110 A | 9/1999 | Patel et al. |
| 5,993,844 A | 11/1999 | Abraham et al. |
| 6,099,567 A | 8/2000 | Badylak et al. |
| 6,171,344 B1 | 1/2001 | Atala |
| 6,206,931 B1 * | 3/2001 | Cook et al. .................. 623/23.75 |
| 6,358,284 B1 | 3/2002 | Fearnot |
| 6,475,232 B1 | 11/2002 | Babbs et al. |
| 6,579,538 B1 | 6/2003 | Spievack |
| 6,666,892 B2 | 12/2003 | Hiles et al. |
| 7,029,434 B2 | 4/2006 | Carpentier et al. |
| 7,652,077 B2 * | 1/2010 | Cook et al. .................... 523/113 |
| 7,699,895 B2 | 4/2010 | Hiles et al. |
| 2001/0048949 A1 | 12/2001 | Atala |
| 2002/0048595 A1 | 4/2002 | Geistlich et al. |
| 2002/0103542 A1 * | 8/2002 | Bilbo ......................... 623/23.72 |
| 2010/0041135 A1 * | 2/2010 | Badylak et al. ................ 435/325 |

(56) References Cited

U.S. PATENT DOCUMENTS

FOREIGN PATENT DOCUMENTS

| WO | WO 85/04413 | 10/1985 | | |
|---|---|---|---|---|
| WO | WO 90/00060 | 1/1990 | | |
| WO | WO 90/00395 | 1/1990 | | |
| WO | WO 93/05798 | 1/1993 | | |
| WO | WO 95/18529 | 7/1995 | | |
| WO | WO 95/22611 | 8/1995 | | |
| WO | WO 96/24661 | 8/1996 | | |
| WO | WO 96/25179 | 8/1996 | | |
| WO | WO 96/31157 | 10/1996 | | |
| WO | WO 96/31225 | 10/1996 | | |
| WO | WO 96/32146 | 10/1996 | | |
| WO | WO 9810775 A1 * | 3/1998 | ............ | A61K 35/37 |
| WO | WO 98/22158 | 5/1998 | | |
| WO | WO 98/25545 | 6/1998 | | |
| WO | WO 98/25636 | 6/1998 | | |
| WO | WO 98/25637 | 6/1998 | | |
| WO | WO 98/26291 | 6/1998 | | |
| WO | WO 00/32250 | 6/2000 | | |

OTHER PUBLICATIONS

European Search Report EP 08008810 dated Jun. 27, 2008.
Hodde, J.P. et al., "Gycosaminoglycan Content of Small Intestinal Submucosa: A Bioscaffold for Tissue Repladement" Tissue Engineering, vol. 2, No. 3, 1996, pp. 209-217 XP002063373.
Hodde, J.P. et al., "Glycosaminoglycan Content of Small Intestinal Submucosa: A Bioscaffold for Tissue Replacement" Tissue Engineering, vol. 2, No. 3, 1996, pp. 209-217, XP002063373.
Probst, M. et al., "Reproduction of functional smooth muscle tissue and partial blader replacement,"British Journal of Urology (1997), 79, 505-515.
Sutherland, Ronald S. et al., "Regeneration of Bladder Urothelium, Smooth Muscle, Blood Vessels and Nerves into an Acellular Tissue Matrix," The Journal of Urology, vol. 156, 571-577, Aug. 1996.
"Chitterlings" http://chitterlings.com/chitterling.html. from Oct. 13, 1999, accessed Sep. 30, 2010; 2 pages.
Acell, Incorporated et al.'s Appeals from the U.S. District Court, ND of Indiana in case No. 4:03CV0046, (Sep. 30, 2005).
Badylak, S.F. et al.: "the Use of Xenogeneic Small Intestinal Submucosa as a Biomaterial for Achille's Tendon Repair in a Dog Model"; Journal of Biomedical Matrials Research, vol. 29, No. 8, 1995, pp. 977-985, XP002071882.
Center for Disease Control and Prevention. Morbidity and Mortality Weekly Report. (1990) 39(45), pp. 819-820.
Cobb, M.S. et al.: "Histology After Dural Grafting With Small Inestinal Submucosa", Surgical Neurology, vol. 46, No. 4, 1996, pp. 389-394, XP00201883.
Cross Appellant Cook Biotech Incorporated's Brief in Support of Cross-Appeal of Judgment of Non-Willfulness, Inventorship and No Relief for Infringement, and in Opposition to Appellants' Markman Appeal, U.S. District Court, ND of Indiana in case No. 4:03CV0046. (Nov. 14, 2005).
Cross-Appellant Purdue Research Foundation's Brief in Support of Cross-Appeal of Judgment, and in Opposition to Appellants' Markman Appeal, U.S. District Court, ND of Indiana in case No. 4:03CV0046, (Nov. 14, 2005).

Defendants' Post-Hearing Markman Memorandum, *Cook Biotech Incorporated et al. v. ACell et al.*, USDC ND IN Case No. 4:03CV0046, (Aug. 16, 2004).
Judgment, U.S. Court of Appeals, U.S. District Court ND of Indiana, Case No. 4:03-CV-0046 (Aug. 18, 2006).
Memorandum and Order, *Cook Biotech Incorporated et al. v. ACell et al.*, USDC ND IN Case No. 4:03CV0046, (Aug. 31, 2004).
Ornitz, David M. et al., "Fibroblast growth factors," Genome Biology 2001, 2(3):reviews 3005.1-3005.12.
Plaintiffs'Post-Hearing Markman Brief, *Cook Biotech Incorporated et al. v. ACell et al.*, USDC ND IN Case No. 4:03CV0046, (Aug. 16, 2004).
Reply and Answering Brief of Defendants-Appellants to Cross Appeal Briefs of Plaintiffs-Cross-Appellants Cook Biotech Incorporated and Purdue Research Foundation, U.S. District Court, ND of Indiana in case No. 4:03CV0046, (Dec. 22, 2005).
Vaught, J.D. et al.; "Detrusor Regeneration in the Rat Using Porcine Small Intestinal Submucosal Grafts: Functional Innervation and Receptor Expression", The Journal of Urology, vol. 155, No. 1, 1996, pp. 374-378, XP002071884.
"Guideline on Validation of the Limulus Amebocyte Lysate Test as an End-Product Endotoxin Test for Human and Animal Parenteral Drugs, Biological Products, and Medical Devices". Dec. 1997. Ctr for Drug Evaluation & Research, Ctr for Biologic Evaluation & Research, Ctr for Devices & Radiological Health and Ctr for Veterinary Medicine.
American National Standard, ANSI/AAMI 10993-1:1994. "Biological Evaluation of Medical Devices—Part 1: Guidance on Selection of Tests". Association for the Advancement of Medical Instrumentation. pp. 9-17.
Block, S. "Peroxygen Compounds", Disinfection, Sterilization and Preservation, 5th Edition 2001, pp. 185-204. Lippincott Williams & Wilkins, Philadephia, PA.
Clarke, K.M., et al. "Intestine Submucosa and Polypropylene Mesh for Abdominal Wall Repair in Dogs". The Journal of Surgical Research. Jan. 1996. vol. 60, No. 1. pp. 107-114.
Denton, F.W., "Chlorhexidine", Disinfection, Sterilization and Preservation, S. Block, editor, 5th Edition 2001. pp. 321-336. Lippincott Williams & Wilkins, Philadelphia, PA.
Hawley's Condensed Chemical Dictionary, Eleventh Edition, Van Nostrand Reinhold Company, (1987), pp. 886 and 890.
Kropp, B.P., et al. "Regenerative Urinary Bladder Augmentation Using Small Intestinal Submucosa: Urodynamic and Histopathologic Assessment in Long-Term Canine Bladder Augmentations". The Journal of Urology. Jun. 1996. vol. 155, No. 6, pp. 2098-2104.
Kropp, B.P., et al. "Experimental Assessment of Small Intestinal Submucosa as a Bladder Wall Substitute", Urology. Sep. 1995. vol. 46, No. 3. pp. 396-400.
Prevel, C.D., et al. "Small Intestinal Submucosa: Utilization as a Wound Dressing in Full-Thickness Rodent Wounds". Annals of Plastic. Surgery. Oct. 1995. vol. 35, No. 4. pp. 381-388.
Prevel, C.D., et al. "Small Intestinal Submucosa: Utilization for Repair of Rodent Abdominal Wall Defects". Annals of Plastic. Surgery. Oct. 1995. vol. 35, No. 4. pp. 374-380.
Wikipedia online definition for "collagen" (Dec. 9, 1996).
D Horak et al: Hydrogels in endovascular embolization. III. Radiopaque spherical particles, their preparation and properties: Biomaterials, GB, Elsevier Sciences Publishers BV., Barking, vol. 2, No. 8 Mar. 1, 1987, pp. 142-145.
European Search Report, Patent Application No. 08012454.8, (Sep. 29, 2008).

* cited by examiner

GRAFT PROSTHESIS, MATERIALS AND METHODS

REFERENCE TO RELATED APPLICATIONS

This is a continuation patent application of U.S. patent application Ser. No. 10/811,343, filed Mar. 26, 2004, now U.S. Pat. No. 7,652,077, which is a continuation of U.S. patent application Ser. No. 09/798,441, filed on Mar. 2, 2001, abandoned, which is a divisional of U.S. patent application Ser. No. 08/916,490 filed Aug. 22, 1997, now U.S. Pat. No. 6,206,931, issued Mar. 27, 2001, which claims the benefit of U.S. Patent. Application Ser. Nos. 60/024,542 and 60/024,693, filed on Aug. 23, 1996 and Sep. 6, 1996, respectively.

TECHNICAL FIELD

This invention relates generally to a medical structure and, in particular, to a graft prosthesis, materials, and methods therefor.

BACKGROUND OF THE INVENTION

Tissue implants in a purified form and derived from collagen-based materials have been manufactured and disclosed in the literature. Cohesive films of high tensile strength have been manufactured using collagen molecules or collagen-based materials. Aldehydes, however, have been generally utilized to cross-link the collagen molecules to produce films having high tensile strengths. With these types of materials, the aldehydes may leech out of the film, e.g. upon hydrolysis. Because such residues are cytotoxic, the films are poor tissue implants.

Other techniques have been developed to produce collagen-based tissue implants while avoiding the problems associated with aldehyde cross-linked collagen molecules. One such technique is illustrated in U.S. Pat. No. 5,141,747 wherein the collagen molecules are cross-linked or coupled at their lysine epsilon amino groups followed by denaturing the coupled, and preferably modified, collagen molecules. The disclosed use of such collagen material is for tympanic membrane repair. While such membranes are disclosed to exhibit good physical properties and to be sterilized by subsequent processing, they are not capable of remodeling or generating cell growth or, in general, of promoting regrowth and healing of damaged or diseased tissue structures.

In general, researchers in the surgical arts have been working for many years to develop new techniques and materials for use as implants and grafts to replace or repair damaged or diseased tissue structures, for example, blood vessels, muscle, ligaments, tendons and the like. It is not uncommon today, for instance, for an orthopedic surgeon to harvest a patellar tendon of autogenous or allogenous origin for use as a replacement for a torn cruciate ligament. The surgical methods for such techniques are known. Further, it has been common for surgeons to use implantable prostheses formed from plastic, metal and/or ceramic material for reconstruction or replacement of physiological structures. Yet, despite their wide use, surgical implanted prostheses present many attendant risks to the patient.

Researchers have also been attempting to develop satisfactory polymer or plastic materials to serve as such functional tissue structures and/or other connective tissues, e.g., those involved in hernia and joint dislocation injuries. It has been discovered that it is difficult to provide a tough, durable plastic material which is suitable for long term connective tissue replacement. The tissues surrounding the plastic material can become infected and difficulties in treating such infections often lead to the failure of the implant or prostheses.

As mentioned above, various collagen-based materials have also been utilized for the above-mentioned tissue replacements; however, these materials either did not exhibit the requisite tensile strength or also had problems with infection and other immunogenic responses, encapsulation, or had other problems when they may have been loaded with antibiotics, growth factors and the like. For example, U.S. Pat. No. 4,956,178 discloses a submucosa collagen matrix which is obtained from the intestinal tract of mammals; however, it is disclosed that the collagen matrix is loaded with antibiotics. In a related patent, U.S. Pat. No. 5,372,821, it is disclosed that a submucosa collagen matrix may be sterilized by conventional techniques, e.g., aldehyde tanning, propylene oxide, gamma radiation and peracetic acid. No specific processing steps are disclosed except that the submucosa layer is first delaminated from the surrounding tissue prior to sterilization treatment.

Therefore, there is a need to obtain improved purified forms of collagen-based matrices from tissue sources thereof. Also, there is a need to provide a process whereby the ease of removal of such matrices from tissue sources is enhanced so as to yield such improved, purified products. The present invention is addressed to these needs.

SUMMARY OF THE INVENTION

In accordance with one preferred embodiment of the present invention, provided is a graft prosthesis which includes a purified, collagen-based matrix structure removed from a submucosa tissue source, wherein the purified structure has a contaminant level making the purified structure biocompatible.

Another preferred embodiment of the invention provides a graft prosthesis which includes a purified, collagen-based matrix structure removed from a submucosa tissue source, wherein the purified structure has an endotoxin level of less than 12 endotoxin units per gram.

Another preferred embodiment of the invention provides a graft prosthesis which includes a purified, collagen-based matrix structure removed from a submucosa tissue source, wherein the purified structure has a nucleic acid content level of less than 2 micrograms per milligram.

Another preferred embodiment of the invention provides a graft prosthesis including a purified, collagen-based matrix structure removed from a submucosa tissue source, wherein the purified structure has a virus level of less than 500 plaque forming units per gram.

The present invention also provides a graft prosthesis which includes a purified, collagen-based matrix structure removed from a submucosa tissue source, wherein the purified structure has a processing agent level of less than 100,000 parts per million per kilogram.

A further embodiment of the invention concerns a method for obtaining a collagen-based matrix from a submucosa tissue source. The method includes treating the submucosa tissue source with a disinfecting agent to provide a disinfected submucosa tissue source, and removing the collagen-based matrix from the disinfected submucosa tissue source.

Another preferred embodiment of the invention provides a method for obtaining a collagen-based matrix from a submucosa tissue source, which includes providing a submucosa tissue source which has been treated with a disinfecting agent, and removing the collagen-based matrix from the submucosa tissue source.

The present invention also concerns a composition which includes a collagen-containing structure removed from a tissue source initially containing the structure and other tissue, wherein the collagen-containing structure has an endotoxin level of no greater than 12 endotoxin units per gram.

Also provided by the present invention is a purified collagen-containing matrix obtained from a mammalian tissue source, the matrix including mammalian tela submucosa and being obtainable by a process which includes disinfecting the mammalian tissue source then removing the structure from the resulting disinfected mammalian tissue source.

In preferred aspects, the invention provides purified forms of tela submucosa collagen matrices derived from the alimentary, respiratory, urinary or genital tracts of animals, the matrices having a bioburden level of substantially zero, and/or being essentially free of pyrogens. A preferred collagen matrix is capable of being implanted within a human or animal patient without causing a cytotoxic response, infection, rejection of the implant or any other harmful effect in a majority of patients. While a preferred implantable collagen matrix according to some aspects of the present invention comprises primarily tela submucosa, the collagen matrix in this instance may also comprise partial layers of laminar muscularis mucosa, muscularis mucosa, lamina propria, a stratum compactum layer and/or other such tissue materials depending upon the source from which it was derived.

Further in accordance with the present invention, a purified delaminated tela submucosa collagen matrix is provided which is derived from the alimentary, respiratory, urinary or genital tracts of animals or humans, wherein said purified submucosa collagen matrix is produced by delaminating a disinfected tela submucosa source to obtain the delaminated tela submucosa collagen matrix. An advantageous matrix may be obtained, for example, by a process comprising treating an unprocessed, undelaminated tela submucosa source harvested from the alimentary, respiratory, urinary or genital tracts of animals with a disinfecting agent, followed by delaminating the tela submucosa collagen matrix from the attached tissues. The preferred collagen matrix has a bioburden level of substantially zero and capable of being implanted within a human or animal patient without causing a cytotoxic response, infection, rejection of the implant or any other harmful effect in a majority of patients.

Still further in accordance with the present invention, a method is provided for obtaining a highly pure, delaminated tela submucosa collagen matrix in a substantially sterile state, comprising delaminating a disinfected tela submucosa tissue source to obtain the delaminated tela submucosa collagen matrix. A preferred method comprises treating an undelaminated tela submucosa source harvested from the alimentary, respiratory, urinary or genital tracts of animals or humans with a disinfecting agent, followed by delaminating the tela submucosa from its other source tissues attached to the tela submucosa.

Still further in accordance with the present invention, provided is a highly pure tela submucosa collagen matrix derived from the alimentary, respiratory, urinary or genital tracts of animals having a bioburden of substantially zero, and wherein said tela submucosa collagen matrix contains substantially no surface debris, e.g. including substantially no muscle tissue, mucosal layers, lipids or cellular debris. The preferred collagen matrix is capable of being implanted within a human or animal patient without causing cytotoxic response, infection, rejection of the implant or any other harmful effect to the patient.

Still further in accordance with the present invention, a highly pure tela submucosa is provided which is derived from the alimentary, respiratory, urinary or genital tracts of animals and wherein the tela submucosa is delaminated in a substantially sterile condition comprising growth factors, and is produced by rinsing the delaminated, tela submucosa source with a solvent, for instance water, followed by treatment with a disinfecting agent, preferably a peracid, at a pH of about 1.5 to about 10 followed by delamination of the tela submucosa from the attached tissues. The peracid is buffered at pH levels greater than 7. Desirably, collagen matrices so produced have a substantial high content of one or more growth factors.

Still further in accordance with the present invention, provided is a tissue graft composition which includes a tela submucosa collagen matrix which is essentially pyrogen free. More preferred such compositions will include a tela submucosa collagen matrix which has a pyrogen content of about 1 endotoxin unit per gram (EU/g) or less.

Still further in accordance with the present invention, a highly pure, tela submucosa as described above, will demonstrate active angiogenesis in vivo upon implantation in a human or animal patient.

This invention relates to purified, implantable tissue constructs, a process for producing such purified, implantable tissue constructs, and their use to promote regrowth and healing of damaged or diseased tissue structures. More particularly, the invention is directed to purified forms of tela submucosa collagen matrix suitable for use as an implantable tissue, and methods for producing such purified forms of this collagen-based implantable tissue.

These and other aspects of the present invention will become apparent to those skilled in the art upon reviewing the specification that follows.

DETAILED DESCRIPTION

For the purpose of promoting an understanding of the principles of the invention, reference will now be made to certain preferred embodiments thereof and specific language will be used to describe the same. It will nevertheless be understood that no limitation of the scope of the invention is thereby intended, such alterations, further modifications and applications of the principles of the invention as described herein being contemplated as would normally occur to one skilled in the art to which the invention relates.

In the discussions herein, a number of terms are used. In order to provide and clear and consistent understanding of the specification and claims, the following definitions are provided.

Bioburden—refers to the number of living microorganisms, reported in colony-forming units (CFU), found on and/or in a given amount of material. Illustrative microorganisms include bacteria, fungi and their spores.

Disinfection—refers to a reduction in the bioburden of a material.

Sterile—refers to a condition wherein a material has a bioburden such that the probability of having one living microorganism (CFU) on and/or in a given section of the material is one in one-million or less.

Pyrogen—refers to a substance which produces febrile response after introduction into a host.

Endotoxin—refers to a particular pyrogen which is part of the cell wall of gram-negative bacteria. Endotoxins are continually shed from the bacteria and contaminate materials.

Purification—refers to the treatment of a material to remove one or more contaminants which occur with the material, for instance contaminants with which the material occurs in nature, and/or microorganisms or components thereof occurring on the material. Illustratively, the contaminants may be those known to cause toxicity, infectivity, pyrogenicity, irritation potential, reactivity, hemolytic activity, carcinogenicity and/or immunogenicity.

Biocompatibility—refers to the ability of a material to pass the biocompatibility tests set forth in International Standards Organization (ISO) Standard No. 10993 and/or the U.S. Pharmacopeia (USP) 23 and/or the U.S. Food and Drug Administration (FDA) blue book memorandum No. G95-1, entitled "Use of International Standard ISO-10993, Biological Evaluation of Medical Devices Part-1: Evaluation and Testing." Typically, these tests assay as to a material's toxicity, infectivity, pyrogenicity, irritation potential, reactivity, hemolytic activity, carcinogenicity and/or immunogenicity. A biocompatible structure or material when introduced into a majority of patients will not cause an adverse reaction or response. In addition, it is contemplated that biocompatibility can be effected by other contaminants such as prions, surfactants, oligonucleotides, and other biocompatibility effecting agents or contaminants.

Contaminant—refers to an unwanted substance on, attached to, or within a material. This includes, but is not limited to: bioburden, endotoxins, processing agents such as antimicrobial agents, blood, blood components, viruses, DNA, RNA, spores, fragments of unwanted tissue layers, cellular debris, and mucosa.

Tela submucosa—refers to a layer of collagen-containing connective tissue occurring under the mucosa in most parts of the alimentary, respiratory, urinary and genital tracts of animals.

As disclosed above, the present invention generally provides graft prostheses and materials including a purified collagen-based matrix structure, and methods for obtaining and using the same. Advantageous graft prostheses of the invention are obtained from a submucosa tissue source, for example including animal tissues such as human or other mammalian tissues, e.g. porcine, bovine or ovine tissues.

Tela submucosa, as with many animal tissues, is generally aseptic in its natural state, provided the human or animal does not have an infection or disease. This is particularly the case since the tela submucosa is an internal layer within the alimentary, respiratory, urinary and genital tracts of animals. Accordingly, it is generally not exposed to bacteria and other cellular debris such as the epithelium of the intestinal tract. One feature of the present invention is the discovery that by disinfecting the source tissue for the tela submucosa prior to delamination, the aseptic state of the tela submucosa layer can be preserved or substantially preserved, particularly if the delamination process occurs under sterile conditions.

In particular, it has been discovered that disinfecting the tela submucosa source, followed by removal of a purified matrix including the tela submucosa, e.g. by delaminating the tela submucosa from the tunica muscularis and the tunica mucosa, minimizes the exposure of the tela submucosa to bacteria and other contaminants. In turn, this enables minimizing exposure of the isolated tela submucosa matrix to disinfectants or sterilants if desired, thus substantially preserving the inherent biochemistry of the tela submucosa and many of the tela submucosa's beneficial effects.

A tela submucosa implantable collagen matrix according to the present invention can, as indicated above, be obtained from the alimentary, respiratory, urinary or genital tracts of animals. Preferably, the tela submucosa tissues, which are collagen-based and thus predominantly collagen, are derived from the alimentary tract of mammals and most preferably from the intestinal tract of pigs. A most preferred source of whole small intestine is harvested from mature adult pigs weighing greater than about 450 pounds. Intestines harvested from healthy, nondiseased animals will contain blood vessels and blood supply within the intestinal tract, as well as various microbes such as *E. coli* contained within the lumen of the intestines. Therefore, disinfecting the whole intestine prior to delamination of the tela submucosa substantially removes these contaminants and provides a preferred implantable tela submucosa tissue which is substantially free of blood and blood components as well as any other microbial organisms, pyrogens or other pathogens that may be present. In effect, this procedure is believed to substantially preserve the inherent aseptic state of the tela submucosa, although it should be understood that it is not intended that the present invention be limited by any theory.

It is also desirable that the collagen matrix according to the present invention be substantially free of any antibiotics, antiviral agents or any antimicrobial type agents which may affect the inherent biochemistry of the matrix and its efficacy upon implantation. In the past, one method of treating such tissue material is to rinse the delaminated tissue in saline and soak it in an antimicrobial agent, for example, as disclosed in U.S. Pat. No. 4,956,178. While such techniques can optionally be practiced with isolated submucosa of the present invention, preferred processes according to present invention avoid the use of antimicrobial agents and the like which may not only affect the biochemistry of the collagen matrix but also can be unnecessarily introduced into the tissues of the patient.

As discussed above, it has been discovered that a highly pure form of an implantable tela submucosa collagen matrix may be obtained by first disinfecting a tela submucosa source prior to removing a purified collagen matrix including the tela submucosa layer, e.g. by delaminating the tela submucosa source. It has also been discovered that certain processing advantages as well as improved properties of the resultant tela submucosa layer are obtained by this process, including greater ease in removing attached tissues from the submucosa layer, and a characteristic, low contaminant profile.

Processes of the invention desirably involve first rinsing the tela submucosa source one or more times with a solvent, suitably water. The rinsing step is followed by treatment with a disinfecting agent. The disinfecting agent is desirably an oxidizing agent. Preferred disinfecting agents are peroxy compounds, preferably organic peroxy compounds, and more preferably peracids. Such disinfecting agents are desirably used in a liquid medium, preferably a solution, having a pH of about 1.5 to about 10, more preferably a pH of about 2 to about 6, and most preferably a pH of about 2 to about 4. In methods of the present invention, the disinfecting agent will generally be used under conditions and for a period of time which provide the recovery of characteristic, purified submucosa matrices as described herein, preferably exhibiting a bioburden of essentially zero and/or essential freedom from pyrogens. In this regard, desirable processes of the invention involve immersing the tissue source (e.g. by submersing or showering) in a liquid medium containing the disinfecting agent for a period of at least about 5 minutes, typically in the range of about 5 minutes to about 40 hours, and more typically in the range of about 0.5 hours to about 5 hours.

A preferred peroxy disinfecting agent is hydrogen peroxide. The concentration of hydrogen peroxide can range from about 0.05% to 30% by volume. More preferably the hydrogen peroxide concentration is from about 1% to 10% by volume and most preferably from about 2% to 5% by volume. The solution may or may not be buffered to a pH from about 5 to 9. More preferably the pH is from about 6 to 7.5. These concentrations can be diluted in water or in an aqueous solution of about 2% to about 30% by volume alcohol. Most preferably the alcohol is ethanol. The solution temperature can range from about 15 to 50° C. More preferably the solution temperature is from about 20 to 40° C. Most preferably, the solution temperature is from about 32 to 37° C. The exposure time can range from about 10 to 400 minutes. Preferably, the exposure time is from about 120 to 240 minutes. More preferably, the exposure time is from 180 to 210 minutes.

A preferred organic peroxide disinfecting agent is perpropionic acid. The concentration of perpropionic acid may range from about 0.1% to 10% by volume. More preferably the perpropionic acid concentration is from about 0.1% to 1.0% by volume and most preferably from about 0.2% to 0.5% by volume. These concentrations of perpropionic acid can be diluted in water or in an aqueous solution of about 2% to about 30% by volume alcohol. Most preferably the alcohol is ethanol. The tela submucosa tissue source can be exposed to the organic peroxide solution for periods from about 15 minutes to about 40 hours, and more typically in the range of about 0.5 hours to about 8 hours. Other peroxy disinfecting agents are suitable for use as described in "Peroxygen Compounds", S. Block, in *Disinfection, Sterilization and Preservation*, S. Block, Editor, 4th Edition, Philadelphia, Lea & Febiger, pp. 167-181, 1991; and "Disinfection with peroxygens", M. G. C. Baldry and J. A. L. Fraser, in *Industrial Biocides*, K. Payne, Editor, New York, John Wiley and Sons, pp. 91-116, 1988.

Another oxidizing disinfecting agent is chlorhexidine (1,6-di(4-chlorophenyldiguanido)hexane) in its digluconate form. The concentration of chlorhexidine digluconate may range from about 0.1% to 15% by weight. More preferably, the chlorhexidine digluconate concentration is from about 0.1% to 2% by weight and most preferably from about 0.2% to 5% by weight. The solution may or may not be buffered to a pH from about 5 to 8. More preferably the pH is from about 5.5 to 7. These concentrations may be diluted in water or in an aqueous solution of about 2% to about 20% by volume alcohol. Most preferably the alcohol is ethanol at a concentration of about 5% to 10%. The solution temperature may range from about 15 to 30° C. The exposure time may range from about 10 to 400 minutes. More preferably the exposure time is from about 30 to 60 minutes. Other chlorine agents are described in "Chlorhexidine", G. W. Denton, in *Disinfection, Sterilization and Preservation*, S. Block, Editor, 4th Edition, Philadelphia, Lea & Febiger, pp. 274-289, 1991.

In preferred preparative processes, a peracid or other disinfecting agent may be dissolved in a dilute aqueous alcohol solution, preferably wherein the alcohol has from 1 to about 6 carbon atoms, and wherein the alcohol may generally comprise from about 1% to about 30% by volume of the solution. More preferred alcohols for use in the invention are selected from the group consisting of ethanol, propanols and butanols. Ethanol is a most preferred alcohol for these purposes.

When a peracid is used in the disinfection, it is preferably selected from the group consisting of peracetic acid, perpropionic acid or perbenzoic acid. Peracetic acid is the most preferred disinfecting agent. The peracetic acid is preferably diluted into about a 2% to about 10% by volume alcohol solution. The concentration of the peracetic acid may range, for example, from about 0.05% by volume to about 1.0% by volume. Most preferably the concentration of the peracetic acid is from about 0.1% to about 0.3% by volume. Hydrogen peroxide can also be used as a disinfecting agent. Alternatively, or in addition, the tela submucosa tissue source, e.g. from small intestine, may be disinfected utilizing disinfecting agents such as glutaraldehyde, formalin and the like, which are also known for their ability to introduce substantial crosslinking into collagen matrices, in contrast to the action of other disinfecting agents such as peracids which can be used to disinfect without introducing such crosslinking. Additionally, the tela submucosa source can be treated with radiation, e.g., gamma radiation, for purposes of disinfection.

Variations on the disinfection process can also include the following:
1. Intestine is treated with 0.2% peracetic acid, 5% ethanol solution at a ratio of 10:1 solution to intestine ratio by weight. Solution has a pH of 2.6. Solution and intestine are vigorously mixed for two hours.
2. Intestine is treated with 1% peracetic acid, 25% ethanol solution at a ration of 5:1 solution to intestine ratio by weight. Solution has a pH of 2. Solution and intestine are vigorously mixed for one hour.
3. Intestine is treated with 1% peracetic acid, 15% ethanol, and 10% hydrogen peroxide solution at a ratio of 5:1 solution to intestine ratio by weight. Solution and intestine are vigorously mixed for one hour.
4. Whole small intestine is rinsed four times with high purity water for 15 minutes. The intestine is then subjected to 1.5 MRAD Electron Beam radiation.
5. Whole small intestine is rinsed four times with high purity water for 15 minutes. Lengthwise along a conveyor belt, the intestine is subjected to high-intensity pulsed light which disinfects the intestine.

Following the treatment as described above, the tela submucosa layer is delaminated from its source, e.g., whole intestine, cow uterus and the like. It has been found that by following this post-disinfection-stripping procedure, it is easier to separate the tela submucosa layer from the attached tissues, e.g. at least from attached tunica muscularis tissue, as compared to stripping the tela submucosa layer prior to disinfection. Moreover it has been discovered that the resultant tela submucosa layer in its most preferred form exhibits superior histology, in that there is less attached tissue and debris on the surface compared to a tela submucosa layer obtained by first delaminating the tela submucosa layer from its source and then disinfecting the layer. Moreover, a more uniform tela submucosa tissue can be obtained from this process, and a tela submucosa having the same or similar physical and biochemical properties can be obtained more consistently from each separate processing run. Importantly, a highly purified, substantially sterile tela submucosa is obtained by this process.

The stripping of the tela submucosa source is preferably carried out by utilizing a disinfected or sterile casing machine, to produce a tela submucosa which is substantially sterile and which has been minimally processed. A suitable casing machine is the Model 3-U-400 Stridhs Universal Machine for Hog Casing, commercially available from the AB Stridhs Maskiner, Götoborg, Sweden. Therefore, the measured bioburden levels are minimal or substantially zero. Of course, other means for delaminating the tela submucosa source can be employed without departing from the present invention, including for example delaminating by hand.

It has also been discovered that more preferred processes according to the present invention, not only will eliminate or significantly reduce contaminants contained in the tela submucosa collagen matrix, but also will produce a tissue which exhibits no substantial degradation of physical and mechanical properties, e.g., differential porosity (i.e. wherein one side of the submucosa layer has greater porosity than the other side), and good strength, for example burst strength. Also, it has been discovered that more preferred processes do not affect the differential porosity of the tela submucosa collagen matrix which ultimately affects the level of efficacy of this tissue implant. For example, the tissue is not necessarily treated with a crosslinking agent or a material that disrupts the porosity or inherent, native structure of the collagen matrix. Moreover, when hydrogen peroxide is employed, the matrix as a whole has greater porosity as well as a higher oxygen content. This helps to ensure the absence of contaminants e.g., endotoxins, pyrogens and the like.

Also, in an advantageous form, the collagen-based matrices of the present invention (e.g., including tela submucosa) demonstrate the ability to induce active angiogenesis, i.e., an ingrowth of blood vessels within the matrix of the tissue. In this regard, these preferred matrices of the invention will contain beneficial components with which the matrices naturally occur, including for example one or more of glycosaminoglycans, glycoproteins, proteoglycans, and/or growth factors (e.g. Transforming Growth Factor-á, Transforming Growth Factor-â, and/or Fibroblast Growth Factor 2 (basic)).

Preferred collagen-based matrices of the invention, preferably submucosa-containing matrices, are also characterized by the low contaminant levels set forth in Table 1 below, each contaminant level taken individually or in any combination with some or all of the other disclosed contaminant levels. The abbreviations in Table 1 are as follows: CFU/g=colony forming units per gram; PFU/g=plaque forming units per gram; ìg/mg=micrograms per milligram; ppm/kg=parts per million per kilogram.

TABLE 1

| FEATURE | FIRST PREFERRED LEVEL | SECOND PREFERRED LEVEL | THIRD PREFERRED LEVEL |
|---|---|---|---|
| ENDO-TOXIN | <12 EU/g | <10 EU/g | <5 EU/g |
| BIOBUR-DEN | <2 CFU/g | <1 CFU/g | <0.5 CFU/g |
| FUNGUS | <2 CFU/g | <1 CFU/g | <0.5 CFU/g |
| NUCLEIC ACID | <10 µg/mg | <5 µg/mg | <2 µg/mg |
| VIRUS | <500 PFU/g | <50 PFU/g | <5 PFU/g |
| PROCESS-ING AGENT | <100,000 ppm/kg | <1,000 ppm/kg | <100 ppm·kg |

Even more preferred collagen-based matrices of the invention contain an endotoxin level of less than 1 EU/g, and most preferably less than 0.5 EU/g.

Figure 1:
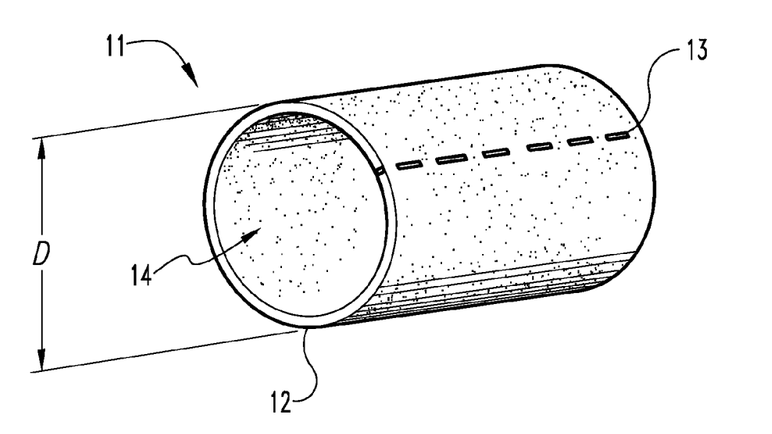
FIG. 1 provides a perspective view of a tubular graft prosthesis structure in accordance with the invention.

Purified collagen-based matrices according to the present invention may be processed in a number of ways, to provide collagenous matrices useful both in vitro and in vivo. For example, the submucosa may be configured to provide tissue grafts useful in vascular applications, e.g. as generally described in U.S. Pat. Nos. 2,127,903 and 4,902,508. With reference now to FIG. 1, for use in vascular grafting, a generally tubular graft prosthesis structure 11 is formed with or including the collagen-based matrix 12, the diameter "D" of which approximates that of a recipient blood vessel. In one mode, this may be accomplished by manipulating a tubular segment or sheet of the tela submucosa to define a cylinder having a diameter "D" approximately the same as that of the recipient blood vessel, and suturing, bonding or otherwise securing the longitudinal seam 13 to form an appropriately-dimensioned tubular vascular graft having a lumen 14 for passage of blood. In illustrative preparative procedures, the graft is formed over a sterile rod or mandrel having an outer diameter approximately equal to that of the vessel to be grafted. For instance, the rod is introduced into the lumen of a tela submucosa segment retaining its native, tubular form. Redundant tissue is then gathered, and the desired lumen diameter achieved by suturing along the length of the graft (for example, using two continuous suture lines or a simple interrupted suture line), or by using other art-recognized tissue securing techniques. Alternatively, a sheet of the inventive tela submucosa is wrapped about the rod to form an overlapping seam, which can be sutured, glued or otherwise secured, to provide the tubular graft construct. In preferred forms, the inner, luminal surface of the graft can be formed by the mucosal side of the tela submucosa.

The tela submucosa of the invention possesses mechanical properties highly desirable for tissue graft materials in vascular applications, including low porosity index, high compliance, and a high burst strength. One skilled in the art will appreciate that the preferred tissue graft material will be of low enough porosity to prevent intraoperative hemorrhage and yet of high enough porosity to allow extension of a newly-developed vasa vasorum through the graft material to nourish the neointima and luminal surface.

Tela submucosa tissue of the present invention can also be processed to provide fluidized compositions, for instance using techniques as described in U.S. Pat. No. 5,275,826. In this regard, solutions or suspensions of the tela submucosa can be prepared by comminuting and/or digesting the tela submucosa with a protease (e.g. trypsin or pepsin), for a period of time sufficient to solubilize the tissue and form substantially homogeneous solution. The submucosa starting material is desirably comminuted by tearing, cutting, grinding, shearing or the like. Grinding the submucosa in a frozen or freeze-dried state is advantageous, although good results can be obtained as well by subjecting a suspension of pieces of the submucosa to treatment in a high speed blender and dewatering, if necessary, by centrifuging and decanting excess waste. The comminuted tela submucosa can be dried, for example freeze dried, to form a powder. Thereafter, if desired, the powder can be hydrated, that is, combined with water or buffered saline and optionally other pharmaceutically acceptable excipients, to form a fluid tissue graft composition, e.g. having a viscosity of about 2 to about 300,000 cps at 25EC. The higher viscosity graft compositions can have a gel or paste consistency.

Fluidized tela submucosa of this invention finds use as an injectable heterograft for tissues, for example, bone or soft tissues, in need of repair or augmentation most typically to correct trauma or disease-induced tissue defects. The present fluidized submucosa compositions are also used advantageously as a filler for implant constructs comprising, for example, one or more sheets of tela submucosa formed into sealed (sutured) pouches for use in cosmetic or trauma-treating surgical procedures.

In one illustrative preparation, tela submucosa prepared as described herein is reduced to small pieces (e.g. by cutting) which are charged to a flat bottom stainless steel container. Liquid nitrogen is introduced into the container to freeze the specimens, which are then comminuted while in the frozen state to form a coarse tela submucosa powder. Such processing can be carried out, for example, with a manual arbor press with a cylindrical brass ingot placed on top of the frozen specimens. The ingot serves as an interface between the specimens and the arbor of the press. Liquid nitrogen can be added periodically to the tela submucosa specimens to keep them frozen.

Other methods for comminuting tela submucosa specimens can be utilized to produce a tela submucosa powder usable in accordance with the present invention. For example, tela submucosa specimens can be freeze-dried and then ground using a manual arbor press or other grinding means. Alternatively, tela submucosa can be processed in a high shear blender to produce, upon dewatering and drying, a tela submucosa powder.

Further grinding of the tela submucosa powder using a prechilled mortar and pestle can be used to produce consistent, more finely divided product. Again, liquid nitrogen is used as needed to maintain solid frozen particles during final grinding. The powder can be easily hydrated using, for example, buffered saline to produce a fluidized tissue graft material of this invention at the desired viscosity.

To prepare another preferred fluidized material, a tela submucosa powder can be sifted through a wire mesh, collected, and subjected to proteolytic digestion to form a substantially homogeneous solution. For example, the powder can be digested with 1 mg/ml of pepsin (Sigma Chemical Co., St. Louis Mo.) and 0.1 M acetic acid, adjusted to pH 2.5 with HCl, over a 48 hour period at room temperature. After this treatment, the reaction medium can be neutralized with sodium hydroxide to inactivate the peptic activity. The solubilized submucosa can then be concentrated by salt precipitation of the solution and separated for further purification and/or freeze drying to form a protease-solubilized intestinal submucosa in powder form.

Fluidized tela submucosa compositions of this invention find wide application in tissue replacement, augmentation, and/or repair. The fluidized submucosal compositions can be used to induce regrowth of natural connective tissue or bone in an area of an existent defect. By injecting an effective amount of a fluidized submucosa composition into the locale of a tissue defect or a wound in need of healing, one can readily take advantage of the biotropic properties of the tela submucosa.

It is also possible to form large surface area constructs by combining two or more tela submucosa segments of the invention, for instance using techniques as described in U.S. Pat. No. 2,127,903 and/or International Publication No. WO 96/32146, dated 17 Oct. 1996, publishing International Application No. PCT/US96/04271, filed 5 Apr. 1996. Thus, a plurality of tela submucosa strips can be fused to one another, for example by compressing overlapping areas of the strips under dehydrating conditions, to form an overall planar construct having a surface area greater than that of any one planar surface of the individual strips used to form the construct.

Tela submucosa of the invention can also be employed to prepare tissue graft constructs useful in orthopedic soft tissue applications, for example in tendon or ligament repair, employing techniques in the art which have been applied to other naturally-derived or synthetic graft materials. For instance, repair techniques as generally described in U.S. Pat. Nos. 2,127,903 and 5,281,422 can be undertaken using tela submucosa of the present invention.

For tendon and ligament replacement applications, a segment of the tela submucosa can be preconditioned by longitudinal stretching to an elongated length. For example, a tela submucosa segment can be conditioned by the prolonged application of a load on the longitudinal axis of the segment (e.g. by suspending a weight from the segment) for a period of time sufficient to allow about 10% to about 20% elongation of the tissue segment. The graft material can also be preconditioned by stretching in the lateral dimension. The tela submucosa segment can then be configured, alone or in combination with other segments, to a variety of shapes to serve as a ligament or tendon replacement, or to substitute for or patch a broken or severed tendon or ligament.

For such connective tissue grafting applications, the segment is desirably configured to have a layered or multilayered configuration, with at least the opposite end portions and/or opposite lateral portions being formed to have multiple layers of the graft material to provide reinforcement for attachment to physiological structures such as bone, tendon, ligament, cartilage and muscle. In a ligament replacement application, opposite ends will be attached to first and second bones, respectively, the bones typically being articulated as in the case of a knee joint. In a tendon replacement application, a first end of the graft construct will be attached to a bone, and a second end will be attached to a muscle.

As indicated above, in connective tissue applications, it will be advantageous to form, manipulate or shape the end portions of the graft construct to be attached, for example, to a bone structure, in a manner that will reduce the possibility of graft tearing at the point of attachment. For these purposes, the tela submucosa graft material can be folded or partially everted to provide multiple layers for gripping, for example, with spiked washers or staples. Alternatively, a tela submucosa segment can be folded back on itself to join the end portions to provide a first connective portion to be attached, for example, to a first bone and a bend in the intermediate portion to provide a second connective portion to be attached to a second bone articulated with respect to the first bone.

For example, one of the end portions of the tela submucosa graft can be adapted to be pulled through a tunnel in, for example, the femur and attached thereto, while the other of the end portions may be adapted to be pulled through a tunnel in the tibia and attached thereto to provide a substitute for the natural cruciate ligament, the segment being adapted to be placed under tension between the tunnels to provide a ligament function, i.e., a tensioning and position function provided by a normal ligament.

Because grafts used in orthopedic applications are typically placed under tension in their surgical installation, it is preferable to combine two or even more tissue segments to provide a multi-ply (multi-layered) graft construct. It is another object of the present invention, therefore, to provide such grafts in which two or more submucosa segments are arranged to have their end portions joined together with the joined end portions and/or lateral portions adapted to be attached to a bone, tendon, ligament or other physiological structure. One method for providing a double segment can be to pull one tubular segment internally within another segment to provide a double-walled tube, the joined ends of which can be attached, for example, to a bone, tendon or ligament. These doubled segments will provide enhanced tensile strength and retela submucosatance to stretching under tension. In other forms, multiple tela submucosa segments or strips can be arranged in a braided configuration, for example a diamond or sashcord braided configuration, or in a mesh configuration including multiple loops intercoupled to neighboring loops, which usefully serve in ligament or tendon repair.

Tela submucosa of the present invention can also be used to provide an orthopedic graft for use as connective tissue to hold fractured bone pieces together and in proper orientation in the body, the tissue segment being formed to serve as a fracture wrap about segments of fractured bone and to be attached to the bone.

In still further orthopedic applications, tela submucosa of the invention can be used to repair bone tissue, for instance using the general techniques described in U.S. Pat. No. 5,641,518. Thus, a powder form of the tela submucosa can be implanted into a damaged or diseased bone region for repair.

The tela submucosa powder can be used alone, or in combination with one or more additional bioactive agents such as physiologically compatible minerals, growth factors, antibiotics, chemotherapeutic agents, antigen, antibodies, enzymes and hormones. Preferably, the powder-form implant will be compressed into a predetermined, three-dimensional shape, which will be implanted into the bone region and will substantially retain its shape during replacement of the graft with endogenous tissues.

Tela submucosa of the invention can also be used as a cell growth substrate, illustratively in sheet, paste or gel form in combination with nutrients which support the growth of the subject cells, e.g. eukaryotic cells such as endothelial, fibroblastic, fetal skin, osteosarcoma, and adenocarcinoma cells (see, e.g. International Publication No. WO 96/24661 dated 15 Aug. 1996, publishing International Application No. PCT/US96/01842 filed 9 Feb. 1996. In preferred forms, the tela submucosa substrate composition will support the proliferation and/or differentiation of mammalian cells, including human cells.

The inventive tela submucosa can also serve as a collagenous matrix in compositions for producing transformed cells, (see, e.g., International Publication No. WO 96/25179 dated 22 Aug. 1996, publishing International Application No. PCT/US96/02136 filed 16 Feb. 1996; and International Publication No. WO 95/22611 dated 24 Aug. 1995, publishing International Application No. PCT/US95/02251 filed 21 Feb. 1995). Such compositions for cell transformation will generally include purified tela submucosa of the present invention, for example in fluidized or paste form, in combination with a recombinant vector (e.g. a plasmid) containing a nucleic acid sequence with which in vitro or in vivo target cells are to be genetically transformed. The cells targeted for transformation can include, for example, bone progenitor cells.

Tela submucosa of the invention can also be used in body wall repair, including for example in the repair of abdominal wall defects such as hernias, using techniques analogous to those described in *Ann. Plast. Surg.*, 1995, 35:3740380; and *J. Surg. Res.*, 1996, 60:107-114. In such applications, preferred tela submucosa tissue grafts of the invention promote favorable organization, vascularity and consistency in the remodeled tissue. In dermatological applications, tela submucosa of the invention can be used in the repair of partial or full thickness wounds and in dermal augmentation using general grafting techniques which are known to the art and literature (see, e.g. Annals of Plastic Surgery 1995, 35:381-388). In addition, in the area of burn treatment, it is generally known to provide a dermal substitute onto which cultured epidermal grafts (preferably cultured epidermal autografts, or CEA's) are transplanted. Such cultured grafts have typically involved transplanting keratinocytes and/or fibroblasts onto the dermal substitute. In accordance with the present invention, the purified tela submucosa can be used as the dermal substitute, for example in sheet form, and the CEA accordingly transplanted onto the tela submucosa. In one mode of practicing this aspect of the invention, keratinocytes can be transplanted, for example by seeding or transferring a keratinocyte sheet, onto the mucosal side of the tela submucosa. Fibroblasts can be transplanted also on the mucosal and/or on the opposite (abluminal) side of the tela submucosa.

Tela submucosa of the invention can also be used in tissue grafting in urogenital applications. For instance, the tela submucosa can be used in urinary bladder repair to provide a scaffold for bladder regeneration, using techniques corresponding to those generally described in U.S. Pat. No. 5,645,860; *Urology*, 1995, 46:396-400; and *J. Urology*, 1996, 155: 2098. In fluidized form, the inventive tela submucosa can also find use in an endoscopic injection procedure to correct vesicureteral reflux. In such applications, a submucosal injection can be made, for instance in the area under the ureteral orifice of a patient, to induce smooth muscle growth and collagen formation at the injection site.

In other areas, tissue graft constructs formed with tela submucosa of the present invention can be used in neurologic applications, for example in techniques requiring a dural substitute to repair defects due to trauma, tumor resection, or decompressive procedures.

In order to promote a further understanding of the present invention and its features and advantages, the following specific Examples are provided. It will be understood that these specific Examples are illustrative, and not limiting, of the present invention.

EXAMPLE 1

Thirty feet of whole intestine from a mature adult hog is rinsed with water. This material is then treated in a 0.2 percent by volume peracetic acid in a 5 percent by volume aqueous ethanol solution for a period of two hours with agitation. The tela submucosa layer is then delaminated in a disinfected casing machine from the whole intestine. The delaminated tela submucosa is rinsed four (4) times with sterile water and tested for impurities or contaminants such as endotoxins, microbial organisms, and pyrogens. The resultant tissue was found to have essentially zero bioburden level. The tela submucosa layer separated easily and consistently from the whole intestine and was found to have minimal tissue debris on its surface.

EXAMPLE 2

A ten foot section of porcine whole intestine is washed with water. After rinsing, this section of tela submucosa intestinal collagen source material is treated for about two and a half hours in 0.2 percent peracetic acid by volume in a 5 percent by volume aqueous ethanol solution with agitation. Following the treatment with peracetic acid, the tela submucosa layer is delaminated from the whole intestine. The resultant tela submucosa is then rinsed four (4) times with sterile water. The bioburden was found to be essentially zero.

EXAMPLE 3

A small section of the tela submucosa intestinal collagen material was subcutaneously implanted in a rat. Within 72 hours, significant angiogenesis was observed.

EXAMPLE 4

Two sections of small intestine are processed by differing methods. The first section is rinsed in tap water, disinfected for 2 hours in a 5% by volume aqueous ethanol solution comprising 0.2% by volume peracetic acid, pH approximately 2.6, delaminated to the tela submucosa, rinsed in purified water, divided into two samples and rapidly frozen. The second section is rinsed in tap water, delaminated to the tela submucosa, rinsed in purified water, placed in a 10% neomycin sulfate solution for 20 minutes (as described in U.S. Pat. No. 4,902,508), rinsed in purified water, divided into two samples and rapidly frozen. The four above-prepared samples are tested for bioburden and endotoxin levels. The first two samples each have bioburdens of less than 0.1 CFU/g and endotoxin levels of less than 0.1 EU/g. The second two samples have respective bioburdens of 1.7 CFU/g and 2.7 CFU/g and respective endotoxin levels of 23.9 EU/g and 15.7 EU/g.

EXAMPLE 5

Three sections of small intestine are processed by differing methods. The first is rinsed in tap water, disinfected for 2 hours in a 5% by volume aqueous ethanol solution comprising 0.2% by volume peracetic acid, pH about 2.6, delaminated to the tela submucosa, rinsed in purified water, and rapidly frozen. The second is rinsed in tap water, delaminated to the tela submucosa, rinsed in purified water, disinfected according to the methods of Example 1 in U.S. Pat. No. 5,460,962 (treatment for 40 hours in a 0.1% by volume aqueous solution of peracetic acid, buffered to pH 7.2), and rapidly frozen. The third is rinsed in tap water, delaminated to the tela submucosa, rinsed in purified water, disinfected according to the methods of Example 2 in U.S. Pat. No. 5,460,962 (treatment in 0.1% by volume peracetic acid in high salt solution, buffered to pH 7.2), and rapidly frozen. All three samples were tested for endotoxins. The endotoxin levels were <0.14 EU/g for the first sample, >24 EU/g for the second sample, and >28 EU/g for the third sample.

EXAMPLE 6

Two sections of porcine small intestine were infected with $7 \times 10^6$ plaque forming units (PFU) of virus. Both were exposed to a 0.18% peracetic acid, 4.8% aqueous ethanol solution at a nine-to-one weight ratio of solution to material. A first sample was immersed in this solution for 5 minutes; the second was immersed for 2 hours. The material processed for 5 minutes exhibited 400 PFU per gram of material. The material processed for 2 hours exhibited zero PFU per gram of material.

EXAMPLE 7

Purified tela submucosa, prepared as described herein, was tested to determine its nucleic acid content. Four samples of material weighing 5 mg each were subjected to DNA/RNA extraction as detailed in the DNA/RNA Isolation Kit by Amersham Lifescience Inc., Arlington Heights, Ill. Nucleic acid quantitation was performed by spectrophotometric determination of solution optical densities at 260 nm and 280 nm. The average nucleic acid content was 1.9 ∀ 0.2 µg per milligram of material.

Small intestinal submucosa, prepared as described by U.S. Pat. No. 4,902,508, was tested to determine its nucleic acid content. Four samples of material weighing 5 mg each were subjected to DNA/RNA extraction as detailed in the DNA/RNA Isolation Kit by Amersham. Nucleic acid quantitation was performed by spectrophotometric determination of solution optical densities at 260 nm and 280 nm. The average nucleic acid content was 2.4 ∀ 0.2 µg per milligram of material.

EXAMPLE 8

Sections of tela submucosa prepared according to the methods described herein were sent to an independent testing laboratory (NamSA, Inc., Northwood, Ohio) for biocompatibility testing as described in the standard ISO 10993. The samples were tested for USP Acute Systemic Toxicity, USP Intracutaneous Toxicity, Cytotoxicity, LAL Endotoxin, material-mediated Pyrogenicity, Direct Contact Hemolysis, and Primary Skin Irritation. The samples passed all tests, indicating that the material is biocompatible.

It will be appreciated that variations of the above-described processing procedures are intended to be within the scope of this invention. For example, the source tissue for the tela submucosa, e.g., stomach, whole intestine, cow uterus and the like, can be partially delaminated, treated with a disinfecting or sterilizing agent followed by complete delamination of the tela submucosa. Illustratively, attached mesentery layers, and/or serosa layers of whole intestine can be advantageously removed prior to treatment with the disinfecting agent, followed by delamination of remaining attached tissues from the tela submucosa. These steps may or may not be followed by additional disinfection steps, e.g., enzymatic purification and/or nucleic acid removal. Alternatively, the tela submucosa source can be minimally treated with a disinfecting or other such agent, the tela submucosa delaminated from the tunica muscularis and tunica mucosa, followed by a complete disinfection treatment to attain the desired contaminant level(s). All such variations and modifications are contemplated to be a part of the process described herein and to be within the scope of the invention.

In addition, it will be appreciated that the publications cited herein are indicative of the skill possessed by those practiced in the relevant field, and each such publication is hereby incorporated by reference in its entirety as if individually incorporated by reference and fully set forth.

What is claimed is:

1. A surgical method for treating a patient, comprising: implanting a multilayer construct in the patient, the multilayer construct including a plurality of layers of tissue matrix material obtained from mammalian urinary tract tissue, wherein each of the layers of tissue matrix material includes submucosa tissue and lamina propria tissue and retains one or more native growth factors in the tissue matrix material, wherein said tissue matrix material is provided in a sterile condition while retaining said one or more native growth factors, and wherein said one or more native growth factors includes Fibroblast Growth Factor-2; and wherein the tissue matrix material additionally retains at least one native bioactive agent selected from the group consisting of a proteoglycan, a glycoprotein, and a glycosaminoglycan.

2. The surgical method of claim 1, wherein said implanting includes applying the multilayer construct to a tissue wall in the body.

3. The surgical method of claim 2, wherein said tissue wall is an abdominal wall.

4. The surgical method of claim 1, wherein said implanting includes applying the multilayer construct to herniated tissue.

5. The surgical method of claim 1, wherein said implanting includes applying the multilayer construct to dermal tissue.

6. The surgical method of claim 1, wherein said implanting includes applying the multilayer construct to urogenital tissue.

7. The surgical method of claim 6, wherein the urogenital tissue is urinary bladder tissue.

8. The surgical method of claim 1, wherein said implanting includes applying the multilayer construct to neurologic tissue.

9. The surgical method of claim 8, wherein the neurologic tissue is dural tissue.

10. The surgical method of claim 1, wherein the tissue matrix material is obtained from a porcine tissue source.

11. The surgical method of claim 1, wherein the tissue matrix material, upon implantation in the patient, promotes regrowth of damaged tissue structures.

12. The surgical method of claim 1, wherein the tissue matrix material additionally retains a proteoglycan, a glycoprotein, and a glycosaminoglycan from the urinary tract tissue.

13. The surgical method of claim 1, wherein the tissue matrix material is remodelable.

14. The surgical method of claim 1, wherein the tissue matrix material has a bioburden level of less than 0.5 colony forming units per gram, a nucleic acid content level of less than 2 micrograms per milligram, a virus level of less than 5 plaque forming unit per gram, and a fungus level of less than 0.5 colony forming units per gram.

15. The surgical method of claim 14, wherein the tissue matrix material has not been treated with a chemical crosslinking agent.

16. The surgical method of claim 1, wherein the tissue matrix material has been sterilized through contact with an aqueous solution containing a peracid.

17. The surgical method of claim 16, wherein the peracid is peracetic acid.

18. The surgical method of claim 1, wherein the tissue matrix material has not been treated with a crosslinking agent.

19. The surgical method of claim 1, wherein the multilayer construct includes a first layer of tissue matrix material fused to a second layer of tissue matrix material.

20. The surgical method of claim 19, wherein the first layer of tissue matrix material has been fused to the second layer of tissue matrix material by compressing overlapping areas of the first layer of tissue matrix material and the second layer of tissue matrix material under dehydrating conditions.

21. A surgical method to repair a tissue structure of a patient, comprising:
implanting a multilayer construct in the body of a patient and in contact with a tissue structure in need of repair, the multilayer construct including a plurality of layers of tissue matrix material obtained from mammalian urinary tract tissue, wherein each of the layers of tissue matrix material includes submucosa tissue and lamina propria tissue, wherein the submucosa tissue has been separated from attached tunica muscularis tissue occurring to the abluminal side of the submucosa tissue in the urinary tract tissue, and wherein the tissue matrix material retains a proteoglycan, a growth factor, a glycoprotein, and a glycosaminoglycan; and, wherein said implanting includes applying the multilayer construct to a tissue wall in the body.

22. The surgical method of claim 21, wherein the tissue matrix material retains Fibroblast Growth Factor-2.

23. A surgical method to repair a tissue structure of a patient, comprising:
implanting a multilayer construct in the body of a patient and in contact with a tissue structure in need of repair, the multilayer construct including a plurality of layers of tissue matrix material obtained from mammalian urinary tract tissue, wherein each of the layers of tissue matrix material includes tissue material from at least a submucosa layer and a lamina propria layer of the urinary tract tissue, the tissue matrix material retaining one or more native growth factors in the tissue matrix material, wherein said tissue matrix material is provided in a sterile condition while retaining said one or more native growth factors, and wherein said one or more native growth factors includes Fibroblast Growth Factor-2; and wherein the tissue matrix material has not been treated with a chemical crosslinking agent.

24. The surgical method of claim 23, wherein the tissue matrix material additionally retains at least one native bioactive agent selected from the group consisting of a proteoglycan, a glycoprotein, and a glycosaminoglycan.

25. The surgical method of claim 23, wherein the tissue matrix material additionally retains a proteoglycan, a glycoprotein, and a glycosaminoglycan from the urinary tract tissue.

* * * * *